United States Patent [19]

Miller

[11] Patent Number: 4,911,157
[45] Date of Patent: Mar. 27, 1990

[54] SELF-REGULATING, HEATED NEBULIZER SYSTEM

[75] Inventor: Kenneth G. Miller, Corona Del Mar, Calif.

[73] Assignee: Pegasus Research Corporation, Costa Mesa, Calif.

[21] Appl. No.: 305,454

[22] Filed: Feb. 1, 1989

Related U.S. Application Data

[63] Continuation-in-part of Ser. No. 137,834, Jan. 7, 1988, abandoned.

[51] Int. Cl.[4] .................... A61M 11/00; A61M 16/16; A61M 16/14

[52] U.S. Cl. .......................... 128/200.21; 128/203.26; 128/203.25; 239/138

[58] Field of Search ..................... 128/200.14, 200.18, 128/200.21, 203.12, 203.16, 203.17, 203.25, 203.26, 203.27, 204.17; 239/137, 138, 338

[56] References Cited

U.S. PATENT DOCUMENTS 4,195,044 3/1980 Miller ................................ 261/142

4,267,974 5/1981 Kienholz et al. ..................... 239/74

4,427,004 1/1984 Miller ............................ 128/200.21

*Primary Examiner*—Edgar S. Burr

*Assistant Examiner*—Kimberly L. Asher

*Attorney, Agent, or Firm*—Dressler, Goldsmith, Shore, Sutker & Milnamow, Ltd.

[57] ABSTRACT

A nebulizer system for producing a humidified and heated breathing gas to be inhaled by a patient undergoing inhalation therapy. The nebulizer system includes a nebulizer module and a heater module affixed to one another and optionally detachably connected to each other. The nebulizer module is connectable to an oxygen source, a liquid water supply, and, through an outlet, to a breathing apparatus. A throat in the system serves to direct an aerosol spray produced in the nebulizer module to a heat transfer element in a conical flow pattern. The heat transfer element is disposed substantially normal to the flow path of the generated aerosol and is in a direct heat transfer relationship with an outer peripheral portion of the conical flow pattern exhausted from the throat. In this manner, a self-regulating heat input is provided by the present nebulizer system.

8 Claims, 3 Drawing Sheets

SELF-REGULATING, HEATED NEBULIZER SYSTEM

RELATED APPLICATIONS

This application is a continuation-in-part of copending application Ser. No. 137,834, filed Jan. 7, 1988, now abandoned.

TECHNICAL FIELD

This invention relates to inhalation therapy devices nd, more particularly, to a nebulizer system for producing a heated aerosol spray.

BACKGROUND OF THE INVENTION

The administration of oxygen to a patient usually has an adverse drying effect on the patient's respiratory system Therefore, various humidifying or nebulizing devices have been used to condition oxygen being administered to a patient by mixing it with water or aqueous solutions.

A typical nebulizer system for inhalation therapy comprises a bottle or like container of sterile liquid, such as water, and a nebulizer assembly. The nebulizer assembly is usually connected to a supply of pressurized oxygen through appropriate throttling valves. As the oxygen flows through an orifice or a venturi device in the nebulizer it creates a negative pressure which draws liquid from the container tube to the nebulizer assembly through a suction and generates an aerosol spray.

The nebulizer assembly admixes the oxygen with the water to produce a humidified oxygen stream which is delivered to a patient through an outlet. The outlet is connected to a delivery hose extending to the patient to be supplied. However, only a small portion of the water drawn to the nebulizer assembly humidifies the oxygen. The majority of the water is returned to the same container from which it was drawn. Most nebulizer systems also use ambient air to dilute the oxygen in the gas stream.

In inhalation therapy, the humidified oxygen flow usually is warmed before it is administered to the patient. U.S. Pat. No. 4,267,974 to Kienholz et al. and my U.S. Pat. No. 4,427,004 to Miller are but two examples of nebulizer systems which warm a humidified oxygen flow before it is administered to a patient.

The Kienholz et al. nebulizer device includes a nebulizer chamber having a throat from which an aerosol spray pattern is emitted in a generally downward path or direction. The Kienholz et al. device also includes a plastic body formed with a well wherein a heater element is provided for heating the water collected in the well which, in turn, introduces water vapor in the gas stream to a patient. The well and heater element are positioned at a location laterally offset from an outlet end of the throat from which the aerosol spray is emitted.

During operation, the heater element of the Keinholz et al. device is immersed in water collected in the well. When the well is filled, overflow is directed back into a water supply bottle through a return tube. The return of water from the well to the supply bottle results in a rising water temperature in the supply bottle which subsequently causes a rising aerosol spray temperature. As will be readily recognized, this condition may result in spray temperature control problems inasmuch as the amount of heat input to the gas stream and the liquid supply is not readily controllable.

My U.S. Pat. No. 4,427,004 discloses a nebulizer device having a tubular core open at its lower end to a water supply bottle. The tubular core is heated to a desired temperature by an electronically controlled heat source. Small liquid droplets emitted from a nebulizer chamber located at a top end of the core impinge against sides of the tubular core and the resulting downwardly flowing sheath of water is vaporized, wholly or in part, to provide heat input to the inhalation gas mixture. The warmed aerosol spray not used as part of the inhalation mixture is immediately returned to the water supply bottle. The return of heated water to the supply bottle makes it difficult to control spray temperature and, thus, the temperature of the humidified gas mixture to the patient.

Moreover, heaters that warm the liquid supply along its path to the aerosol-generating station usually lack sufficient heating capacity to raise the liquid temperature adequately when room air is entrained to dilute the oxygen stream.

In a humidifier system, a heater vaporizes a small reservoir of liquid by boiling within the system. A drawback of these particular heaters is that if the oxygen flow to the humidifier is inadvertently interrupted, the heater may provide too much heat to the reservoir thus overheating the gas stream to be inhaled or otherwise creating a hazardous condition.

As mentioned hereinabove, most nebulizer systems use ambient air to dilute the oxygen content of the gas stream inhaled by the patient. When air is entrained to dilute the oxygen content, total gas flow to the patient is a function of the amount of air entrained. While less heat input will be required to warm the humidified spray at zero entrainment (pure oxygen) as at full entrainment, the heater of the nebulizer system, however, may not always be properly adjusted by the practitioner in the field when the entrainment is modulated. This can result in undesirably high aerosol temperatures.

Neither the Kienholz et al. nor the Miller device provide a self-regulating system which automatically compensates for modulation of ambient air entrainment.

While various advances in the art of inhalation therapy have been made, problems with currently known nebulizer devices remain. In addition to those problems addressed above, known nebulizer systems are typically too expensive to be disposable or are difficult to resterilize and clean after use. Existing nebulizers are also limited in the moisture input they can provide to the oxygen-enriched breathing gas. Moreover, known nebulizing systems have problems in maintaining a particular temperature for the humidified oxygen stream when it is administered to a patient.

Also, commercially available nebulizers are relatively noisy and use more oxygen than is necessary to provide an aerosol inhalation spray. Due to the lack of accuracy of prior art devices and the many variables involved in the inhalation therapy environment, no prior art device to date has proven capable of providing an adequate output of humidified breathable gas having a controlled temperature when administered to he patient.

SUMMARY OF THE INVENTION

The present invention provides a nebulizer system for humidifying and efficiently heating a breathable gas, such as oxygen-supplemented air, to be inhaled by a patient undergoing inhalation therapy while automatically adjusting the heat input to the the gas when the volumetric rate of the gas to be humidified is changed. The nebulizer system of the present invention includes a nebulizer module, a heater module provided with a heat transfer element secured to the nebulizer module, and a liquid receptacle removably attached to the heater module. In a preferred embodiment, the nebulizer system of the present invention offers a sterile, disposable system which isolates the aerosol spray generated within the nebulizer module from a non-sterile, heater surface in a reusable heater module.

The nebulizer module is connectable to an oxygen supply source and, through an outlet, to an inhalation apparatus. The nebulizer module includes a nebulizing chamber wherein pressurized oxygen gas, ambient air, and water are combined to form an aerosol spray which, in turn, impinges upon an annular heat transfer element operably associated with the heater module. The heat transfer element is positioned substantially normal to the flow path of the aerosol spray and vaporizes the water particles impinging thereon.

More specifically, pressurized oxygen is passed to a nozzle which directs an oxygen flow to a nebulizing zone or chamber defined in the nebulizing module. A liquid supply conduit, extending from the liquid receptacle, is provided with a dispensing port or the like which is likewise arranged in the nebulizing zone adjacent to the oxygen nozzle. The oxygen flow from the nozzle powers an atomizing jet to create localized region of negative pressure at the dispensing port so that a liquid stream is drawn from the receptacle, through the supply conduit, and into the nebulizing chamber.

The oxygen flow or stream breaks the liquid flowing from the dispensing port into fine particles or droplets to produce an aerosol spray. Ambient air may be drawn into the nebulizing chamber through an air intake arranged at the upper end of the nebulizer module. The ambient air mixes with the oxygen in the aerosol spray. An air intake regulator, controls the amount of ambient air introduced to the nebulizing chamber to dilute the oxygen flow.

The aerosol spray or mixture generated in the nebulizing chamber is directed downwardly into an axially extended spray directin throat. The aerosol spray is exhausted in a conical flow pattern from a distal end of the throat. The conical flow pattern exhausted from the conduit can be modulated by adjusting the configuration, e.g., length or diameter, of the throat and/or by regulating the amount of ambient air drawn into the nebulizing chamber. That is, the more ambient air introduced into the nebulizing chamber, the greater the total volumetric rate of aerosol flow. A greater aerosol flow rate, in turn, is reflected in relatively larger flow cone being exhausted from the conduit.

The heater module is detachably connected to the nebulizer module in a position beneath the distal or exhaust end of the throat. In one form of the invention, the heater module includes a heater chamber having an annular heat transfer element disposed in the path of aerosol flow exhausted from the conduit. The heat transfer element is provided with a central aperture which is substantially coaxial with the longitudinal axis of the conduit or throat as well as in registry with a central bore in a heater support. The central bore communicates with the liquid container.

The heat transfer element's surface can have any convenient contour. The surface of the heating element contacts, in a direct heat transfer relationship, a predetermined outer peripheral portion of a conical aerosol spray discharged from the throat. Those particles of the aerosol spray which impinge upon the heat transfer element are volatilized to provide the desired amount of latent heat to the gas mixture passing to the patient. The remainder of the aerosol spray coalesces and passes, substantially unheated, into the liquid receptacle through the central bore in the heater support.

The total flow from the nebulizing chamber may be modulated by the amount of air introduced into the nebulizing chamber. As an example, total flow with no air entrainment (i.e., only oxygen and water) averages approximately 7 liters per minute. This flow increases geometrically as the oxygen concentration is diluted b air so that at 28 percent oxygen (full entrainment) the total flow approximates 80 liters per minute. Clearly, not as much heat is required to volatilize the aerosol spray at zero entrainment (pure oxygen) as at full entrainment; thus, the heat output duty of the heat transfer element can vary considerably.

The design contemplated by the present invention provides a self-regulating heat input feature which mitigates the problem of such changing heat requirements. By providing substantial axial alignment between the annular heating element and the throat, the heat output of the heating element is self-regulated as a function of the conical flow pattern exhausted from the throat. Because a smaller size flow cone is exhausted from the conduit or throat as the entrainment of the nebulizer is reduced, fewer aerosol droplets or particles are impinge upon and vaporized by the heat transfer element of the heater. Conversely, as a larger size flow cone is exhausted from the conduit or throat as a result of higher entrainment and, thus, increased total flow, more particles strike the hot surface of the heat transfer element. Therefore, the aerosol spray can be maintained at a substantially constant temperature at widely varying air intake rates to the nebulizer system. As such, a greater heat input to the gas stream is automatically provided to match the higher flow rate.

A modified form of the invention involves a disposable modular system which provides an aseptic barrier between the nebulizer module and the heater module. Such a system includes a sterile, disposable nebulizing head with entrainment capability and entrainment control, a heat transfer element adapted for operable association with a heater, a reusable heater, and a supply of sterile water or an aqueous solution.

The nebulizing head includes a body defining a nebulizing zone at the upper end of the nebulizer body. A rotating closure regulates the amount of ambient air passing through an aperture into the nebulizing zone. As with the first embodiment, an oxygen flow directed to the nebulizing zone powers an atomizing jet of the annular flow type. The oxygen is mixed in the nebulizing chamber with water drawn from the water bottle and an aerosol spray thus produced is downwardly directed into a throat.

The mixture passes through the throat and is exhausted therefrom in a cone-shaped flow pattern. A relatively thin, heated annular metal disc serves as the heat transfer element and is provided at a lower end of the nebulizing body, beneath the throat, and in a plane substantially normal to the flow path of the generated aerosol stream. The metal disc provides two functions. First, the metal disc defines an annular metal surface for heat transfer to the inhalation mixture. Second, the metal disc isolates the aerosol producing area of the nebulizer system from the reusable heater surface while maintaining a stable, therapeutically-adequate heat output.

Notably, the metal disc defines a centrally disposed aperture arranged in substantial axial alignment with the throat extending from the nebulizing chamber. A conduit depends from the nebulizing head. The position of the aperture in the disc relative to the throat offers the self-regulating function to the nebulizer system inasmuch as only the outer portion of the flow cone exhausted from the throat is heated. Efficiency and temperature stability are enhanced by not heating the spray portion that is returned to the reservoir through the central aperture in the heater disc.

The reusable heater includes an annular heater element which preferably surrounds the depending conduit extending from the nebulizing chamber. The reusable heater is mounted to the nebulizer head so that the heater element is positioned against the annular disc and promotes heat transfer therebetween.

The self-regulating feature heat input offered by all embodiments of the present invention solves the problem of how to maintain an aerosol spray at a substantially constant heated temperature regardless of ambient air intake adjustments to the nebulizer system and without elevating the temperature of the liquid contents of the reservoir Moreover, because the entrainment aperture is at the top of the nebulizer module and entrains axially, more effective entrainment is available and the noise produced in the nebulizing zone is muffled. The nebulizer system of the present invention is, therefore, quieter than known systems. Additionally, the annular flow nozzle used with the present invention is more efficient than other nozzles and uses less oxygen. In addition to saving oxygen, there is provided a reduction in the total flow at full dilution which further educes noise levels, water usage, and heating requirements Other features and advantages of the present invention will become readily apparent from the following detailed description, the appended drawings, and the accompanying claims.

DESCRIPTION OF PREFERRED EMBODIMENTS

Figure 1:
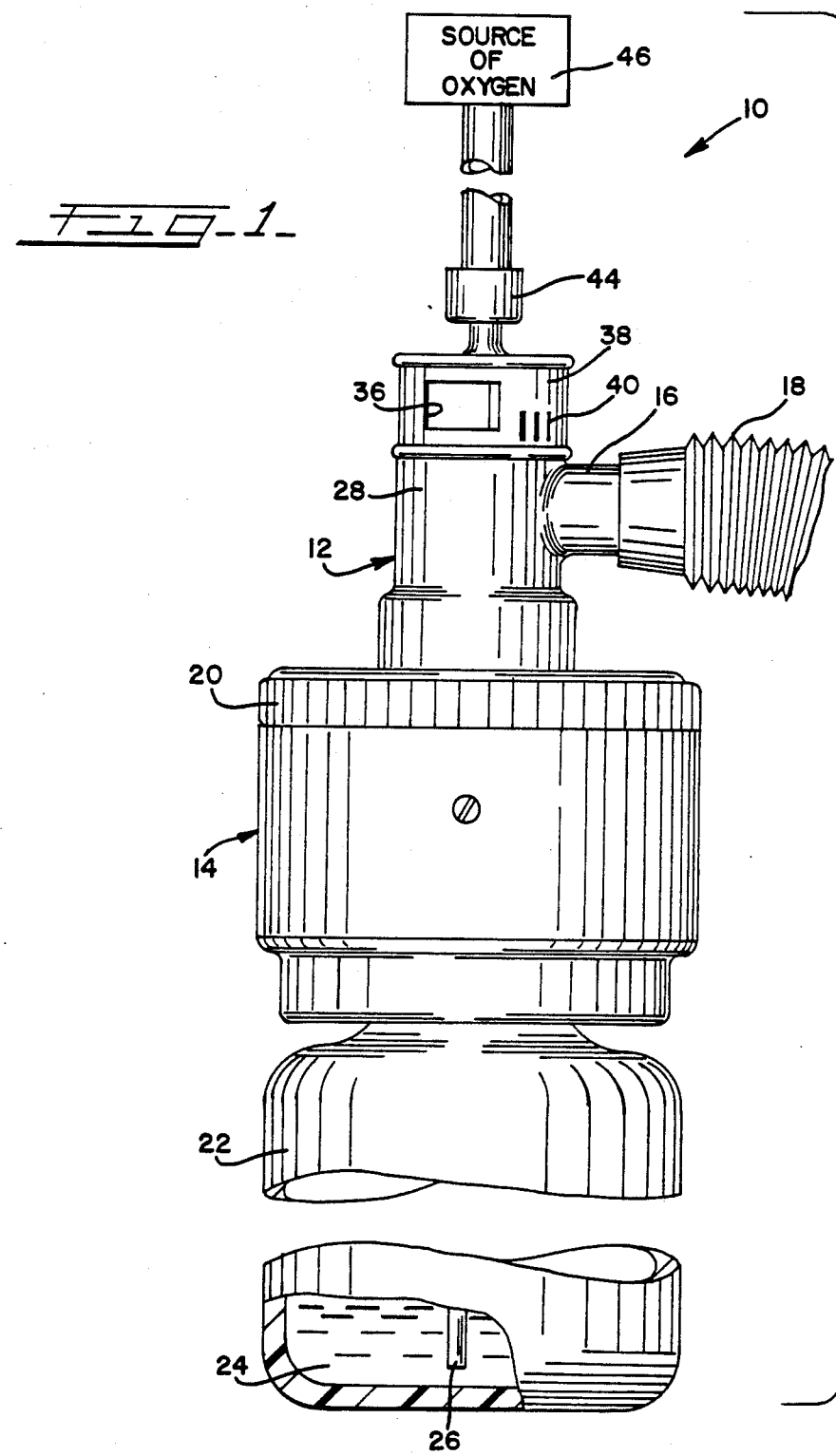
FIG. 1 is an elevational vie, partially broken away to show interior detail, and showing one embodiment of a nebulizer system embodying the principles of the present invention.

While the present invention is susceptible of embodiment in various forms, there are shown in the drawings preferred embodiments hereinafter described, with the understanding that the present disclosure is to be considered as an exemplification of the invention, and is not intended to limit the invention to the specific embodiments illustrated.

Referring now to the drawings, wherein like reference numerals indicate like parts throughout the several views, and in particular to FIG. 1, there is shown a nebulizing device or system 10. The nebulizer device 10 comprises a top section 12 defining a nebulizer module, a detachable heater module 14, and an outlet 16 for connecting the nebulizer apparatus to a breathing apparatus 18. A center section 20 may be used to removably secure the nebulizer module 12 to the heater module 14. The nebulizer device 10 further includes a liquid storing container such as supply bottle 22.

Figure 2:
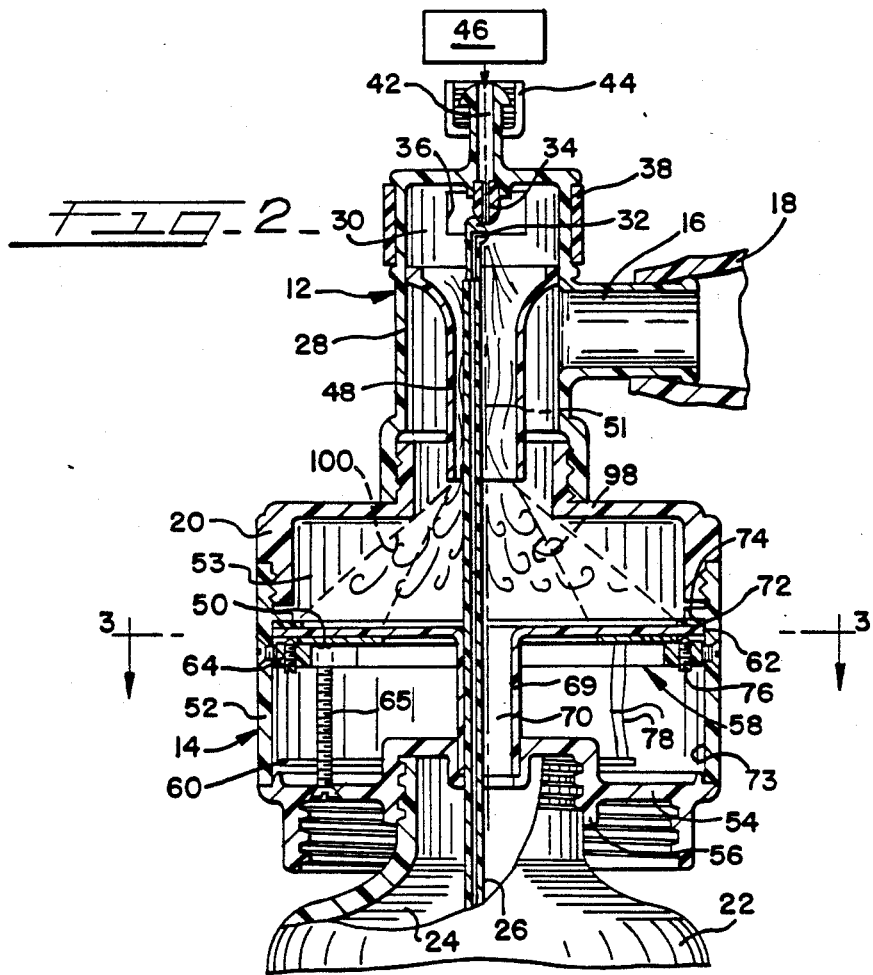
FIG. 2 is an enlarged cross sectional elevational view illustrating an interior of the nebulizer system illustrated in FIG. 1.
Figure 3:
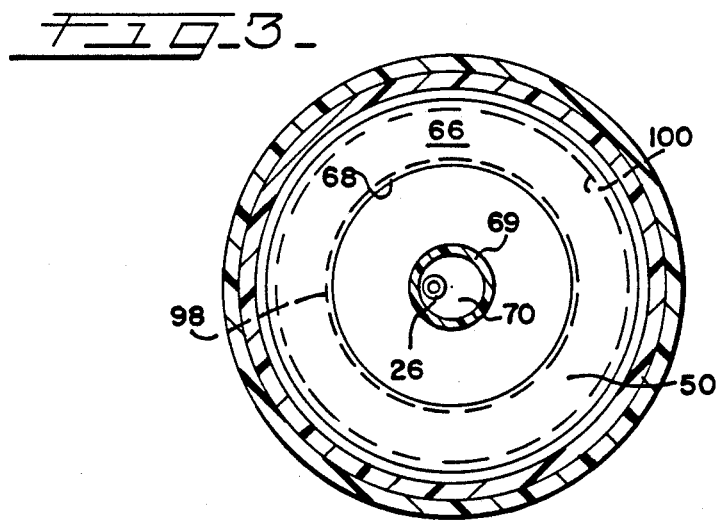
FIG. 3 is a cross sectional plan view taken along plane 3—3 of FIG. 2.

Bottle 22 defines a reservoir 24 adapted to contain a sterile liquid, such as water, which may be medicated, and which is ultimately used to humidify breathable gas for a patient as hereinbelow described. As illustrated in FIG. 2, the supply bottle 22 is attached to the heater module 14 of the nebulizer device 10. Water is delivered to the nebulizer module 14 through a supply conduit 26.

The nebulizer module 12 includes a housing 28 which defines a nebulizer chamber 30. Water supply conduit 26 extends into chamber 30 and terminates in a spray discharge port 32. Similarly, an oxygen nozzle 34 extends into chamber 30 and terminates adjacent to spray discharge port 32. Nozzle 34 and discharge port 32 are positioned in chamber 30 relative to one another so that an oxygen stream exiting nozzle 34 crosses port 32 in a manner generating a relatively lower pressure region within port 32, thereby generating an aerosol spray when liquid water is present in reservoir 24.

Housing 28 further defines an ambient air intake 36 the effective area of which is adjustable by means of regulator ring 38 mounted about the periphery of housing 28. Display indicia 40 may be provided on ring 38 for repeatable settings of air intake area.

Oxygen nozzle 34 communicates with an oxygen feed conduit 42 provided in a connector 44. Connector 44 may be integrally formed with housing 28 and permits attachment of the nebulizer device 10 to a source of pressurized oxygen gas 46.

A hollow, tapering, open-ended throat or conduit 48 is mounted in housing 28. The throat 48 is positioned to receive and shape an aerosol spray generated by the coaction of nozzle 34 an discharge port 32 as will be described in greater detail herein below. Preferably, the dimensions of the conduit 48 are selected to provide a conical aerosol spray having a diameter of about 1½ inches at no ambient air entrainment to about 4 inches at maximum ambient air entrainment at a distance one inch from the distal end of the conduit.

Water supply conduit 26 extends into nebulizer chamber 30 through conduit 48. The proximal end of conduit 48 flares radially outwardly and is adapted to receive the aerosol spray generated in the nebulizing chamber 30. The distal end of conduit 48, on the other hand, extends into the heating chamber 53 of heater module 14 and dispenses the aerosol spray in a cone-shaped configuration onto a planar, annular heating element such as heated disc 50 mounted in the heater module 14. Throat 48 defines a longitudinally extending passageway 51 which defines a flow path for the aerosol spray generated in the nebulizing chamber 30.

The breathable gas outlet 16 is provided in a side wall of nebulizer module 12. The outlet is in communication with an annular space defined by housing 28 and the open-ended throat or conduit 48.

In one form the heater module 14 includes a cylindrical housing 52 which is detachably connected to the nebulizer module beneath the distal end of conduit 48.

As illustrated in FIG. 2, housing 52 together with center section 20 defines a heating chamber 53 and an apertured web 54 through which the supply conduit 26 extends. The web 54 also has a threaded connector portion 56. Connector portion 56 permits attachment of the supply bottle 22 to the heater module 14.

A heater assembly 58 is mounted in the housing 52 of heater module 14. As illustrated, the heater assembly includes the heated annular disc 50, heat input control means 60 for the heated disc, an annular platen 62 positioned over disc 50, and a heat assembly supporting structure for maintaining the heater assembly substantially normal to the flow path of the aerosol stream.

Particularly as illustrated, the heater assembly supporting structure includes an annular support ring 64 disposed in housing 52. The heated annular disc 50 is arranged above the ring 64 and defines a heat transfer element with a heated surface 66. The heated disc 50 is an annularly shaped element having a central aperture 68 substantially aligned with the flow path. Disc 50 can be planar as shown; however, it can also have a toroidal, radially inwardly beveled, wavy, or like configuration as long as the central portion of the conical aerosol spray exiting from conduit 48 remains unheated. The central aperture 68 usually is about 1 to about 2 inches in diameter. As illustrated, the annular platen 62 is arranged above the heated annular disc 50. Alternatively, the heated annular disc can be positioned on the opposite side of platen 62, if desired. A plurality of vertically adjustable members 65 are threadably engaged with the inwardly directed ears defined by ring 64.

The annular platen 62 is concentrically arranged relative to the annular heater disc 50 and defines a tubular extension 69 which extends through the central aperture 68 in the heating element. The tubular extension 69 defines a central port 70 which extends through apertured web 54 of housing 52 and communicates with the liquid reservoir 22. Platen 62 combines with an annular seal ring 72 and a radial projection 74 on housing 52 to define a seal assembly. A series of vertically adjustable members 76 are also threadably engaged with ring 64.

The control means 60 for the heater disc may take the form of a printed circuit board embodying appropriate control circuitry. Control means 60 may be joined or connected to the heated disc 50 through suitable electrical leads 78 to provide the desired electrical energy input thereto. Electrical energy input, usually in the range of about 150 to about 300 watts, is delivered to the disc 50 to provide a latent heat of vaporization input for heating and saturating about 80 liters per minute of breathable gas at 37° C.

In operation, a stream of oxygen is exhausted from the nozzle 34 into the nebulizing chamber. As the oxygen stream passes the discharge port 32 a local negative pressure is generated in the supply conduit 24. This negative pressure draws fluid from bottle 22 into the nebulizing chamber. The liquid water discharged from port 32 admixes with the stream of oxygen to produce an aerosol spray. At the same time, ambient air may be drawn into the nebulizing chamber through the air intake 36 at a predetermined dilution ratio.

The aerosol stream generated in the nebulizing chamber is received by the conduit 48. As the aerosol spray moves toward the distal end of conduit, ambient air may be entrained therewith. The regulator ring 38 may be adjusted to modulate the mix of ambient air and oxygen to achieve the desired oxygen concentration in the inhalation mixture.

The spray is exhausted from the distal end of the conduit in a turbulent, generally conical-shaped flow pattern. The area of heat transfer element 50 is usually selected to allow approximately one-half of the aerosol spray to impinge upon the heated surface 66. That portion of the aerosol spray which avoids impinging on the heated surface coalesces and is conveyed substantially unheated to the reservoir 24 by means of liquid outlet port 70. Only the outer portion of the conical flow pattern strikes the heating surface and is vaporized. The aerosol spray impinging on the heated surface is volatilized as a result, thereby providing heat input to the inhalation mixture. This heated gas mixture is passed to a breathing apparatus through the outlet 16.

To establish good thermal contact between the heat transfer element 50 and platen 62, members 65 on ring 64 may be adjusted in a manner abutting element 50 against platen 62. The other adjustable members 76 on ring 64 urge platen 62 with its tubular extension 69 and seal ring 72 into sealing contact with radial projection 74 defined by housing 52.

By such construction, the heated chamber 53, on one side of platen 62, receives the aerosol mist from the throat 48 while that area o chamber 73 on the opposite side of platen 62 remains substantially "dry". The "dry" camber 73, provides an environment conducive to placement of the control means 60.

Figure 4:
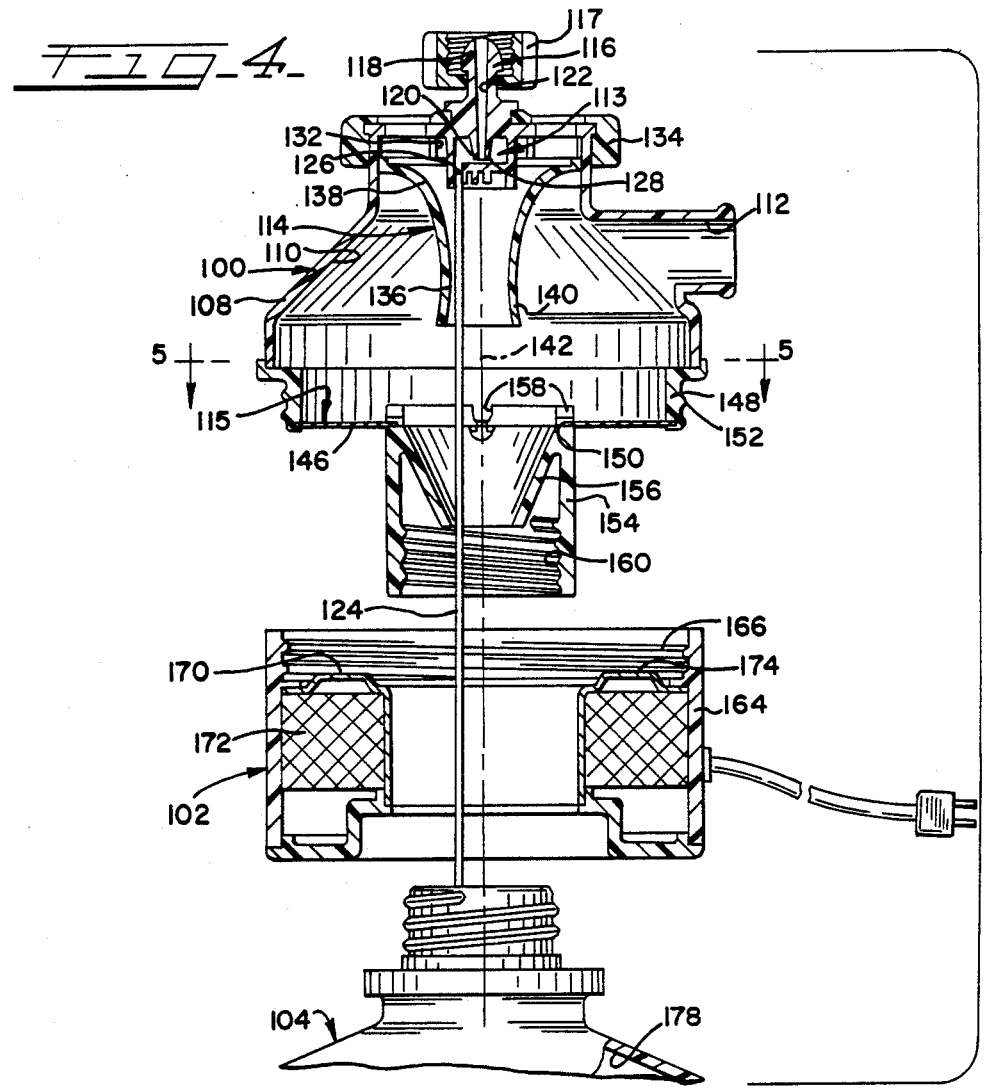
FIG. 4 is an exploded cross sectional elevational view illustrating an interior of a second embodiment of a nebulizer system according to the present invention.
Figure 5:
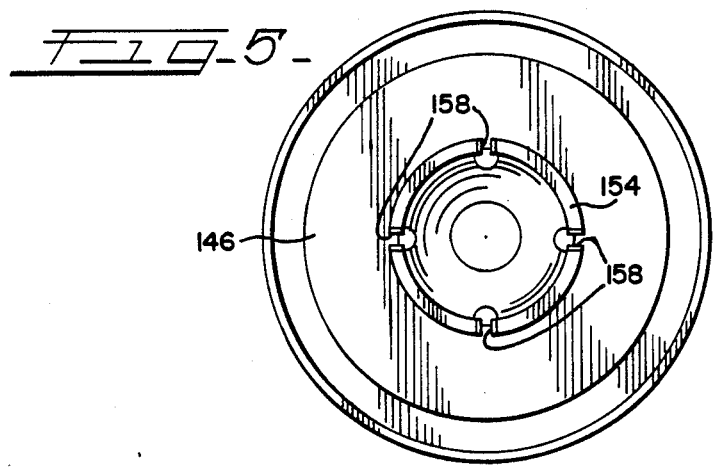
FIG. 5 is a plan view taken along plane 5—5 of FIG. 4.

A disposable, modular nebulizer system embodying the present invention is illustrated in FIGS. 4 and 5. In this particular embodiment, a nebulizer module 100 has releasably secured thereto a heater module 102 and a water supply bottle 104. Nebulizer module 100 is disposable and includes a barrier which provides a sterile environment for the inhalation mixture.

Referring now to FIG. 4, the nebulizer module 100 is comprised of a bodyshell 108 which defines an interior space 110 and a breathing gas outlet 112, a nebulizer means 113, a throat 114 and a heat transfer element 115. The bodyshell 108 preferably is made of a heat sterilizable material. At its upper end, bodyshell 008 defines a nebulizer conduit 116 having a proximal end 118 and a distal end 120. A fluid passage 122 extends longitudinally between the ends of the conduit 116. A liquid supply conduit 124 having a discharge port 126 delivers water to the nebulizer means 113.

The proximal end 118 of the nebulizer conduit 116 defines an attachment means 117 which permits a pressurized gas source (oxygen) to be connected with the fluid passage 122. The distal end 120 of conduit 116 defines a nozzle which is part of nebulizer means 113. During operation, the nozzle creates a relatively low pressure within the supply conduit 124 sufficient to draw water from the supply bottle 104 which is sprayed into the throat 114.

The nebulizer means 113 may be substantially similar to that illustrated in my U.S. Pat. No. 4,427,004. The nebulizer means 113 includes an atomizing jet 128 of the annular flow type which provides a substantially straight path for the resultant aerosol spray through the throat 114.

One advantage of the present invention is its ability to entrain atmospheric air with the aerosol spray. To effect such ends, at its upper end, the bodyshell 108 of nebulizer module 100 defines an air intake opening 132. The air intake opening allows outside ambient air to enter the interior space 110 of the nebulizer. The size of the opening 132, and hence the oxygen concentration in the spray, is controlled by a rotatable regulator 134 carried at the upper end of the bodyshell 108.

Throat 114 includes a hollow, tapering open-ended tube 136 mounted within the nebulizer module 100. Tube 136 is mounted beneath the nebulizer means 113 and is provided with a large end 138, a small end 140 and a longitudinal axis 142. Throat 114 can be a venturi-type device that causes ambient air to be drawn into the nebulizer module for mixing with the aerosol spray. In the preferred embodiment, the discharge from the nebulizer means 113 passes through a hollow portion of the tube 136, thus allowing a straight flow passageway to efficiently mix ambient air with aerosol spray.

The gas outlet 112 is provided in a side wall of the bodyshell 108. The outlet 112 is in communication with the interior space 110 defined by bodyshell 108 and the open-ended throat 114.

The heat transfer element 115 is located at the lower end of the nebulizer module 100, substantially normal to the longitudinal axis 142 of throat 114. As illustrated, heat transfer element 115 includes an annular metal or ceramic disc 146 which i sealed about its peripheral edge to a depending skirt portion 148 defined by bodyshell 108 of module 100. The disc 146 defines a central aperture 150 which is substantially axially aligned with the longitudinal axis 142 of throat 114. For reasons to be described hereinafter, external threading 152 is provided on the skirt portion 148 of the nebulizer module.

The heat transfer element 115 can take the form of an annular, planar disc 146 as shown. Disc 146 can also have, however, a toroidal, radially inwardly beveled, wavy, or like configuration as long as the central portion of the conical flow pattern emitted from throat 114 is allowed to pass through the heat transfer element 115 unheated.

As illustrated, nebulizer module 100 further includes a tubular conduit 154 which is sealed to and concentrically positioned by the central aperture 150 in the disc 146. In a preferred form, and depending from its upper end, conduit 154 defines a funnel like chute 156 which directs unheated water particles in the aerosol spray passing through the central aperture 150 toward the supply bottle 104.

As best illustrated in FIGURE 5, a series of diametrically opposed slots 158 may be provided at the upper end of the conduit 154 to define drain channels for coalesced water formed on dic 146 to feed into the conduit 154 and be directed or returned to the supply bottle. At its lower end, conduit 154 defines an internally threaded portion 160. Notably, the length of tubular conduit 154 is sufficient to pass through the heater module 102 and threadably engage an upper end of the water supply bottle 104 when the modules comprising the nebulizer system are assembled.

Referring again to FIG. 4, the reusable heater module 102 includes a cylindrical housing 164 wnicn is detachably secured to the nebulizer module 100 in a manner permitting the depending tubular conduit 154 to pass therethrough. An upper end of the housing 164 defines an internally threaded portion 166 which coacts with the external threaded portion 152 on the nebulizer module in a manner releasably securing the two modules together.

Heater module 102 further includes a heated platen 170 which overlies an electrically controlled heat source 172 and which defines a heated surface 174. As will be understood, the heated surface 174 of platen 170 is arranged in a heat transfer relationship with the annular disc 146 in the nebulizer module 100 when the heater module 102 is releasably secured to the nebulizer module 100.

The water supply bottle 104 defines a reservoir 178 adapted to contain a sterile liquid, such as water, which may be medicated. As illustrated, the supply bottle 104 is adapted for securement to the internally threaded portion 160 of the conduit 154 and has water removed therefrom through the liquid supply conduit 124.

As mentioned, not as much heat is required at zero entrainment (pure oxygen) as with full entrainment. The heated design presented by the present invention mitigates the heretofor known problems associated with heat control. As mentioned above, a relatively smaller flow cone of aerosol spray is exhausted from the distal end of the throat when the regulator associated with the nebulizer module is adjusted to reduce entrainment. That is, as the entrainment of air in the aerosol spray is reduced, a smaller flow cone results. By providing substantial axial alignment between the annular heat transfer element and the throat, the heat output of the heat transfer element is automatically self-regulated as a function of the conical flow pattern exhausted from the throat.

As the entrainment of air in the aerosol spray is reduced, a smaller flowcone results. As such, fewer aerosol spray particles or droplets are volatilized by the heat transfer element associated with the present invention. Conversely, when the regulator is adjusted to allow more air entrainment with the aerosol flow, the total flow through the throat increases and a relatively larger flow cone or conical flow pattern is exhausted from the distal end of the throat. As such, more particles or droplets of the aerosol spray strike the hot surface of the heat transfer element. Thus, a greater heat output is automatically obtained to match the higher flow rate thereby providing a self-regulating feature for the present invention. In summary,, the aerosol spray is maintained at a substantially constant temperature regardless of the air intake adjustment to the nebulizer system.

If so desired, the nebulizer module, where the aerosol spray is initially produced, can be made as a disposable unit and removably mounted to the reusable heater module. Thus, unlike other units which call for disposal of the entire unit, the nebulizer system of the present invention requires only those parts which are difficult to clean or are not easily sterilized to be disposed of. The provision of the annular disc 146 isolates the nebulizer module from the reusable heater surface while maintaining a stable, therapeutically-adequate heat output.

Because the air intake opening leading to the interior space of the nebulizer module is located at the upper end of the nebulizer, air is entrained with the oxygen flow axially and provides a more effective entrainment plus a reduction in the noise produced by the atomizing jet. The nebulizing system is, therefore, much quieter than other known systems. Provision of an annular flow through the throat is more efficient than other nozzle systems and uses less oxygen. This not only saves oxygen, but reduces the almost unmanageable high total flow at full dilution which further reduces noise levels, water usage and heating requirements.

From the foregoing, it will be observed that numerous modifications and variations can be effected without departing from the true spirit and scope of the novel concept of the present invention. It will be appreciated that the present disclosure is intended as an exemplification of the invention, and is not intended to limit the invention to the specific embodiment illustrated. The disclosure is intended to cover by the appended claims all such modifications as fall within the scope of the claims.

What is claimed is:

1. A heated nebulizer system for a breathing apparatus comprising:
   a nebulizer module connectable to an oxygen supply, said breathing apparatus, and a liquid water supply, said nebulizer module defining a breathing gas outlet port and a nebulizing chamber;
   an aerosol generating means positioned in the nebulizing chamber and adapted for communication with said oxygen supply and with said liquid water supply;
   an elongated, open-ended throat mounted in said nebulizer module for receiving aerosol spray generated in said nebulizing chamber and exhausting the received aerosol spray from said nebulizing chamber in a substantially conical flow pattern;
   a heater module in communication with said nebulizer module;
   a substantially planar annular heat transfer element operably associated with said heater module arranged in a substantially axially aligned relationship with said throat to receive a portion of the exhausted aerosol spray in a direct heat transfer relationship, and positioned substantially normal to the flow path of the exhausted aerosol spray.

2. The nebulizer system of claim 1 further including an air inflow regulating means in said nebulizer module for modulating entrainment of ambient atmospheric air in said aerosol spray.

3. The nebulizer system of claim 1 wherein said heating chamber communicates with the liquid water supply.

4. The nebulizer system of claim 1 wherein the nebulizer module and the heater module are detachably connected to one another, and wherein said heat transfer element is integral with said nebulizer module.

5. The nebulizer system of claim 1 wherein the heater module includes heater control means.

6. A heated nebulizer system for a breathing apparatus comprising:
   a nebulizer module connectable to an oxygen supply, said breathing apparatus, and a sterile liquid water supply, said nebulizer module including a body defining a breathing gas outlet port and a nebulizing zone, said nebulizer module further including an annular heat transfer element provided with a concentric tubular conduit depending therefrom, said conduit defining a threaded portion which permits the sterile waeer supply to be releasably secured thereto;
   an aerosol generating means positioned in the nebulizing zone and adapted for communication with said water supply;
   an elongated, open-ended throat mounted in said nebulizer module in a substantially axially aligned relationship with said annular heating element for receiving aerosol spray generated in said nebulizing zone and exhausting the received aerosol spray from said nebulizing zone in a conical flow pattern such that the outer portion of the flow pattern is volatilized and other portions of the flow pattern are returned unheated to the water supply;
   a heater module including a heated surface arranged in a heat transfer relationship with said annular heat transfer element when said heater module is releasably secured to said nebulizer module, with said tubular conduit of said nebulizer module extending through said heater module and in fluidic communication wit said water supply in a manner isolating an interior of said nebulizer module from the heated surface of said heater module while maintaining a stable, therapeutically-adequate heat output.

7. The heated nebulizer system according to claim 6 wherein said annular heating element is positioned substantially normal to the flow path of the aerosol spray exhausted from said throat.

8. The heated nebulizer system according to claim 6 wherein the body of said nebulizer module defines an aperture at an upper end of said body for allowing ambient air to become axially entrained with oxygen in the nebulizing zone, nd wherein said nebulizer module further defines rotatable means mounted on said body for controlling the size of said aperture.

* * * * *

UNITED STATES PATENT AND TRADEMARK OFFICE
CERTIFICATE OF CORRECTION

PATENT NO. : 4,911,157

DATED : March 27, 1990

INVENTOR(S) : KENNETH G. MILLER

It is certified that error appears in the above-identified patent and that said Letters Patent is hereby corrected as shown below:

```
Col. 3, line 44, "directin" should be -- directing --.
Col. 3, line 53, after "in" (second occurrence) insert -- a --.
Col. 4, line 14, "b" should be -- by --.
Col. 5, line 44, "vie" should be -- view --.
Col. 8, line 24, "o" should be -- or --.
Col. 8, line 26, "camber" should be -- chamber --.
Col. 8, line 41, "008" should be -- 108 --.
Col. 9, line 22, "i" should be -- is --.
Col. 9, line 47, "dic" should be -- disc --.
Col. 9, line 56, "wnicn" should be -- which --.
Col. 10, line 26, "flowcone" should be -- flow cone --.
Col. 10, line 38, "summary,," should be -- summary, --.
Col. 12, line 9, "waeer" should be -- water --.
Col. 12, line 29, "wit" should be -- with --.
Col. 12, line 42, "nd" should be -- and --.
```

Signed and Sealed this

Nineteenth Day of November, 1991

Attest:

HARRY F. MANBECK, JR.

*Attesting Officer*    *Commissioner of Patents and Trademarks*